(12) United States Patent
Rafferty et al.

(10) Patent No.: US 6,316,440 B1
(45) Date of Patent: Nov. 13, 2001

(54) REDUCED DIPEPTIDE ANALOGUES AS CALCIUM CHANNEL ANTAGONISTS

(75) Inventors: Michael Francis Rafferty; Yuntao Song, both of Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/381,983

(22) PCT Filed: Jun. 2, 1999

(86) PCT No.: PCT/US99/12275

§ 371 Date: Sep. 27, 1999

§ 102(e) Date: Sep. 27, 1999

(87) PCT Pub. No.: WO09/38198

PCT Pub. Date: Feb. 10, 2000

Related U.S. Application Data

(60) Provisional application No. 60/094,703, filed on Jul. 30, 1998.

(51) Int. Cl.[7] ........... C07D 295/20; C07D 295/12; C07D 237/20; C07C 237/20; A61K 31/195

(52) U.S. Cl. ........... 514/217.05; 514/183; 514/211.01; 514/217.11; 514/218; 514/227.5; 514/237.5; 514/237.8; 514/252.12; 514/330; 514/423; 514/620; 564/164; 564/165; 540/467; 540/470; 540/483; 540/544; 540/574; 540/607; 540/598; 544/59; 544/168; 544/390; 544/391; 546/245; 548/540; 560/37

(58) Field of Search ............. 540/467, 470, 540/483, 544, 574, 598, 607; 544/59, 168, 390, 391; 546/245; 548/540; 560/37; 564/164, 165; 514/183, 211.1, 217.05, 217.11, 218, 227.5, 237.5, 237.8, 252.12, 330, 423, 620

(56) References Cited

FOREIGN PATENT DOCUMENTS

| 0520200 | 12/1992 | (EP) . |
|---|---|---|
| 94 24116 | 10/1994 | (WO) . |
| 94 27967 | 12/1994 | (WO) . |
| 98 54123 | 12/1998 | (WO) . |

Primary Examiner—Richard L. Raymond
Assistant Examiner—Deepak R. Rao
(74) Attorney, Agent, or Firm—Charles W. Ashbrook; David R. Kurlandsky

(57) ABSTRACT

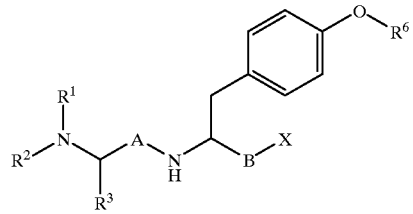

(I)

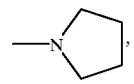

(a)

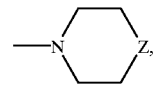

(b)

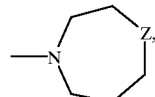

(c)

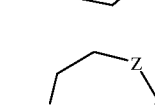

(d)

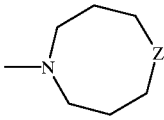

(e)

The present invention provides novel N-type calcium channel blockers, compositions comprising them, and methods of their use. The compounds of the invention are useful in the treatment of stroke, cerebral ischemia, pain, epilepsy, and head trauma. The novel compounds provided by this invention have Formula (1), wherein $R^1$ is H or methyl; $R^2$ is H, azepanylcarbonyl, $C_1$–$C_7$ alkyl, —$(CH_2)_n$-phenyl, wherein the phenyl is unsubstituted or substituted with $C_1$–$C_4$ alkyl, $C_1$–$C_4$ alkoxy, or halo; $R^3$ is $C_1$–$C_5$ alkyl; X is —$NR^4R^5$ or —$OR^7$; $R^4$ and $R^5$ are independently H, $C_1$–$C_5$ alkyl; or $R^4$ and $R^5$ together with the nitrogen to which they are both bound form formulae (a); (b); (c); (d) or (e); $R^6$ is —$(CH_2)_n$-phenyl, wherein the phenyl is unsubstituted or substituted with $C_1$–$C_4$ alkyl, $C_1$–$C_4$ alkoxy, or halo; A and B are independently —CO— or —$CH_2$—, provided that A and B are not both —CO—; $R^7$ is $C_1$–$C_5$ alkyl; Z is —$CH_2$—, —O—, —S—, or —$N(R^8)$—; $R^8$ is H or $C_1$–$C_6$ alkyl; and n is 1 or 2.

7 Claims, No Drawings

REDUCED DIPEPTIDE ANALOGUES AS CALCIUM CHANNEL ANTAGONISTS

This application is a 371 of PCT/US99/12275 filed Jun. 2, 1999 which claims the benefit of U.S. Provisional Application Ser. No. 60/094,703 filed Jul. 30, 1998.

FIELD OF THE INVENTION

The present invention relates to novel compounds, pharmaceutical compositions thereof and methods of using them in the treatment of stroke, cerebral ischemia, pain, epilepsy, and head trauma. In particular, the present invention relates to reduced backbone dipeptide compounds that are potent antagonists of N-type calcium channels.

SUMMARY OF THE RELATED ART

The entry of excessive amounts of calcium ions into neurons following an ischemic episode or other neuronal trauma has been well documented. Uncontrolled high concentrations of calcium in neurons initiate a cascade of biochemical events that disrupts normal cellular processes. Among these events are the activation of proteases and lipases, breakdown of neuronal membranes, and the formation of free radicals, which may ultimately lead to cell death. Several types of calcium channels have been discovered: the L, N, P, Q, R, and T types. Each type possesses distinct structural features, functional properties, and cellular/subcellular distributions. N-type calcium channels are tissue specific, restricted to the central and peripheral neurons of the forebrain and areas rich in synaptic connections. They have well defined roles, e.g., regulation of calcium flux necessary for depolarization-evoked release of transmitter from synaptic endings; and they can be selectively blocked by high-affinity ligands, like ω-conotoxins and synthetic analogs. Bowersox S. S., et al., *Drug News and Perspective*, 1994;7:261–268.

SUMMARY OF THE INVENTION

The present invention provides novel compounds and compositions that are capable of blocking N-type calcium channels. The compounds are useful in a method for treating afflictions associated with increased calcium ion uptake through N-type calcium channels, including such systemic effects as stroke, cerebral ischemia resulting from cardiac arrest, head trauma, closed head injury, pain, and epilepsy. Further advantages of this invention will be clear to one skilled in the art from the reading of the description that follows.

The present invention comprises new compounds and, more particularly, novel reduced backbone dipeptide compounds that are useful as N-type calcium channel blockers in mammals. The novel compounds of the present invention are represented by the following structural Formula I:

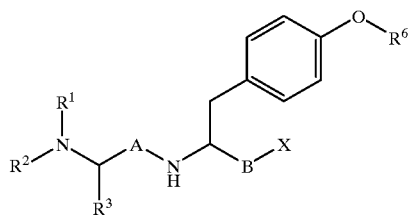

I wherein A, B, X, $R^1$, $R^2$, $R^3$, and $R^6$ are defined in more detail below and generally form a reduced dipeptide backbone.

The invention also includes novel compositions of matter containing the above-defined compound that are useful as neuroprotective agents for the treatment of afflictions associated with increased calcium ion uptake through N-type calcium channels in mammals, as well as the methods of treatment using such compositions.

The foregoing merely summarizes certain aspects of the present invention and is not intended, nor should it be construed, as limiting the invention in any manner. All patents and other publications referenced herein are hereby incorporated by reference in their entirety.

DETAILED DESCRIPTION OF THE INVENTION

The present invention comprises novel reduced backbone dipeptide compounds and pharmaceutical compositions thereof that are useful as N-type calcium channel antagonists.

The novel compounds of the present invention have the following generic structural Formula I:

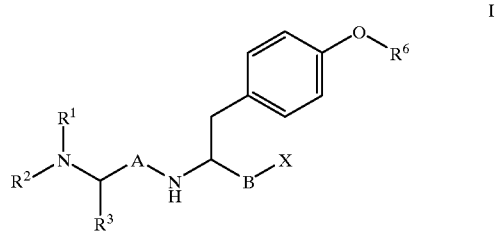

I wherein
$R^1$ is H or methyl,
$R^2$ is H, azepanylcarbonyl, $C_1$–$C_7$ alkyl, —$(CH_2)_n$-phenyl, wherein the phenyl is unsubstituted or substituted with $C_1$–$C_4$ alkyl, $C_1$–$C_4$ alkoxy, or halo,
$R^3$ is $C_1$–$C_5$ alkyl,
X is —$NR^4R^5$ or —$OR^7$,
$R^4$ and $R^5$ are independently H, $C_1$–$C_5$ alkyl, or
$R^4$ and $R^5$ together with the nitrogen to which they are both bound form:

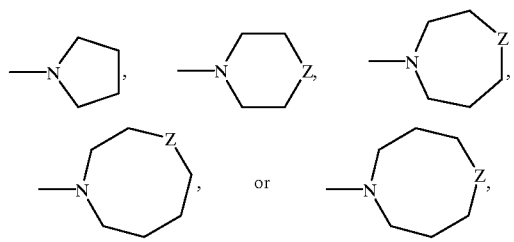

$R^6$ is —$(CH_2)_n$-phenyl, wherein the phenyl is unsubstituted or substituted with $C_1$–$C_4$ alkyl, $C_1$–$C_4$ alkoxy, or halo,
A and B are independently —CO— or —$CH_2$—, provided that A and B are not both —CO—,
$R^7$ is $C_1$–$C_5$ alkyl,
Z is —$CH_2$—, —O—, —S—, or —$N(R^8)$—,
$R^8$ is H or $C_1$–$C_6$ alkyl, and
n is 1 or 2.
In a preferred embodiment of the compound of Formula I, $R^4$ and $R^5$ are independently H, $C_1$–$C_5$-alkyl, or R[4] and R[5] taken together with the nitrogen to which they are both bound form 1-pyrrolidinyl, 1-piperidinyl, or 1-azepanyl, or R[4] and R[5] taken together with the nitrogen to which they are both bound are:

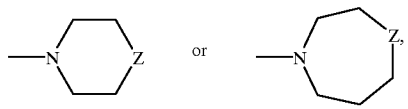

and Z is —S— or —O—.

Also provided are pharmaceutically acceptable salts, esters, amides, and pro-drugs of the compounds of the Formula I.

The term "alkyl" means a straight or branched chain hydrocarbon. Representative examples of alkyl groups are methyl, ethyl, propyl, isopropyl, isobutyl, butyl, tert-butyl, sec-butyl, pentyl, hexyl, $(CH_3)_2CHCH_2CH_2—$, $(CH_3)_3CCH_2CH_2—$, and heptyl.

The term "alkoxy" means an alkyl group attached to an oxygen atom. Representative examples of alkoxy groups include methoxy, ethoxy, tert-butoxy, propoxy, and isobutoxy.

In a preferred embodiment, compounds of the invention are selected from the group consisting of:

2-((2-(Azaperhydroepinylcarbonylamino)-4-methylpentyl) amino)-N-(tert-butyl)-3-(4-(phenylmethoxy)phenyl)-(2S)-propanamide;

[S-(R*,R*)]-Azepane-1-carboxylic acid {1-[2-(4-benzyloxy-phenyl)-1-tert-butoxymethyl-ethylcarbamoyl]-3-methyl-butyl}-amide;

[S-(R*,R*)]Azepane-1-carboxylic acid (1-{[2-(4-benzyloxy-phenyl)-1-tert-butylcarbamoyl-ethylamino]-methyl}-3-methyl-butyl)-amide;

[S-(R*,R*)]-2-Dimethylamino-4-methyl-pentanoic acid [2-(4-benzyloxy-phenyl)-1-morpholin-4-ylmethyl-ethyl]-amide;

[S-(R*,R*)]-Azepane-1-carboxylic acid {1-[2-(4-benzyloxy-phenyl)-1-morpholin-4-ylmethyl-ethylcarbamoyl]-3-methyl-butyl}-amide;

[S-(R*,R*)]Azepane-1-carboxylic acid {1-[2-(4-benzyloxy-phenyl)-1-(tert-butylamino-methyl)-ethylcarbamoyl]-3-methyl-butyl}-amide;

(S,S)-Azepane-1-carboxylic acid{1-[2-(4-benzyloxy-phenyl)-1-diethylaminomethyl-ethylcarbamoyl]-3-methyl-butyl}-amide;

(S)-2-(2-Amino-4-methyl-pentylamino)-3-(4-benzyloxy-phenyl)-N-tert-butyl-propionamide dihydrochloride; and 2-(2-Amino-4-methyl-pentylamino)-3-(4-benzyloxy-phenyl)-N-tert-butyl-propionamide dihydrochloride.

The compounds of the invention may be readily prepared as set forth in the following reaction scheme(s) which employ general synthetic methods well-known to those skilled in organic chemistry. The following definitions apply:

| | |
|---|---|
| $H_2SO_4$ | Sulfuric acid |
| HBTU | O-benzotriazol-1-yl-N,N,N',N'-tetramethyluronium-hexafluorophosphate |
| DMAP | 4-(Dimethylamino)pyridine |
| DMF | N,N-Dimethylformamide |
| $Et_2O$ | Diethylether |
| HCl | Hydrochloric acid |
| $NaBH_3CN$ | Sodium cyanoborohydride |
| MeOH | Methanol |
| TFA | Trifluoroacetic acid |
| DMC | 4,4'-Dichloro-α-methylbenzhydrol |
| i-$Pr_2$Net | Diisopropyl ethylamine |
| LAH | Lithium aluminum hydride |
| HNMeOMe | Methoxymethylamine |
| Pd/C | Palladium on carbon catalyst |

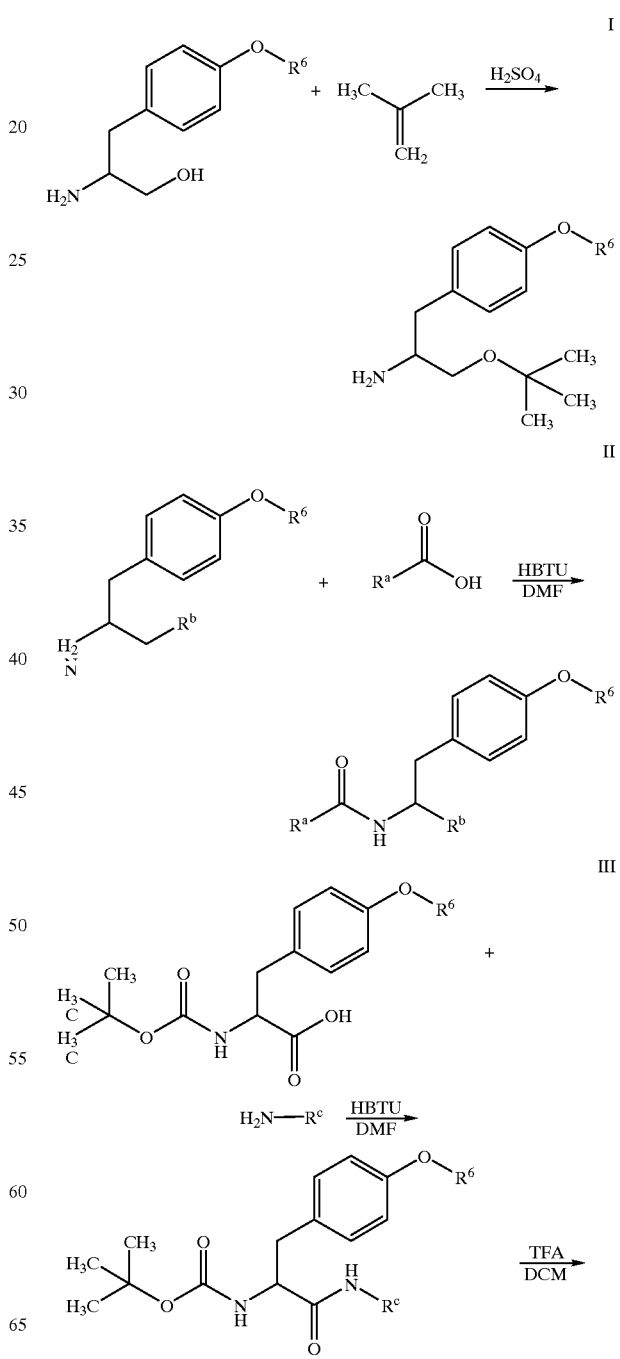

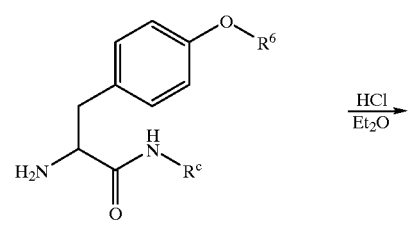
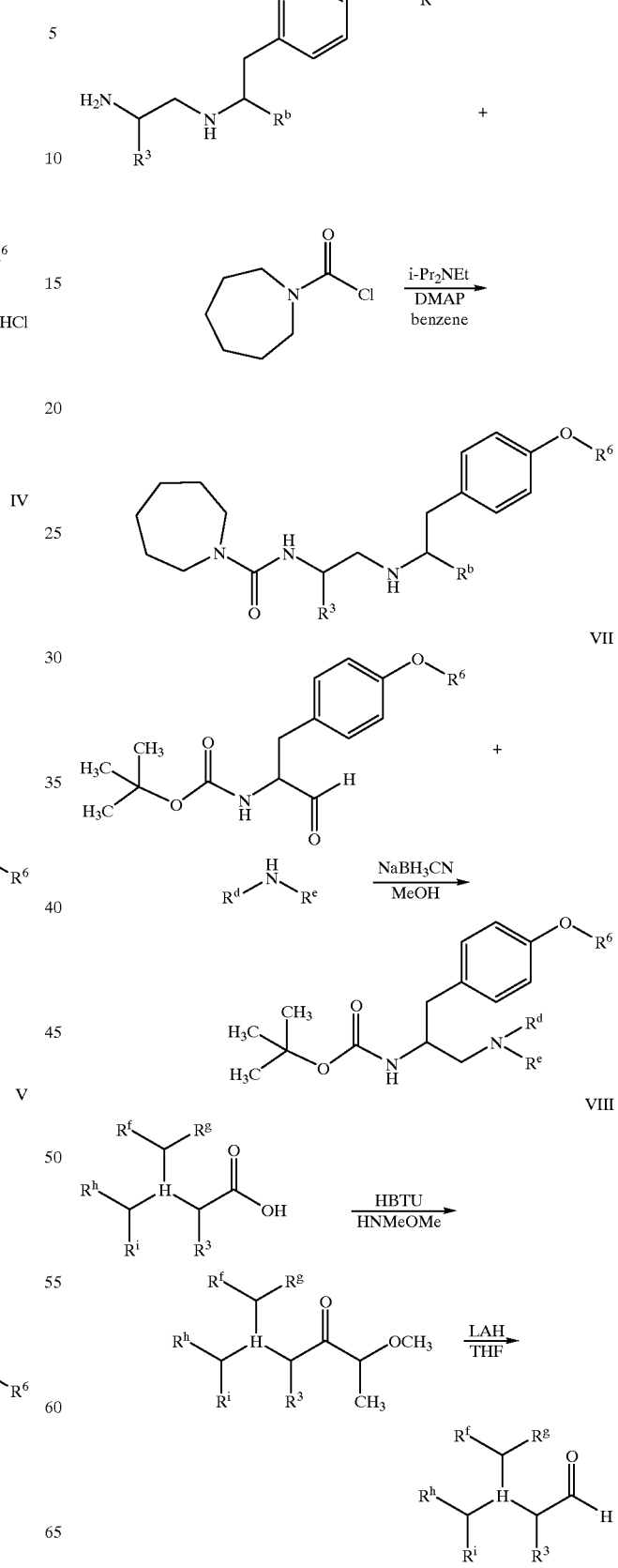

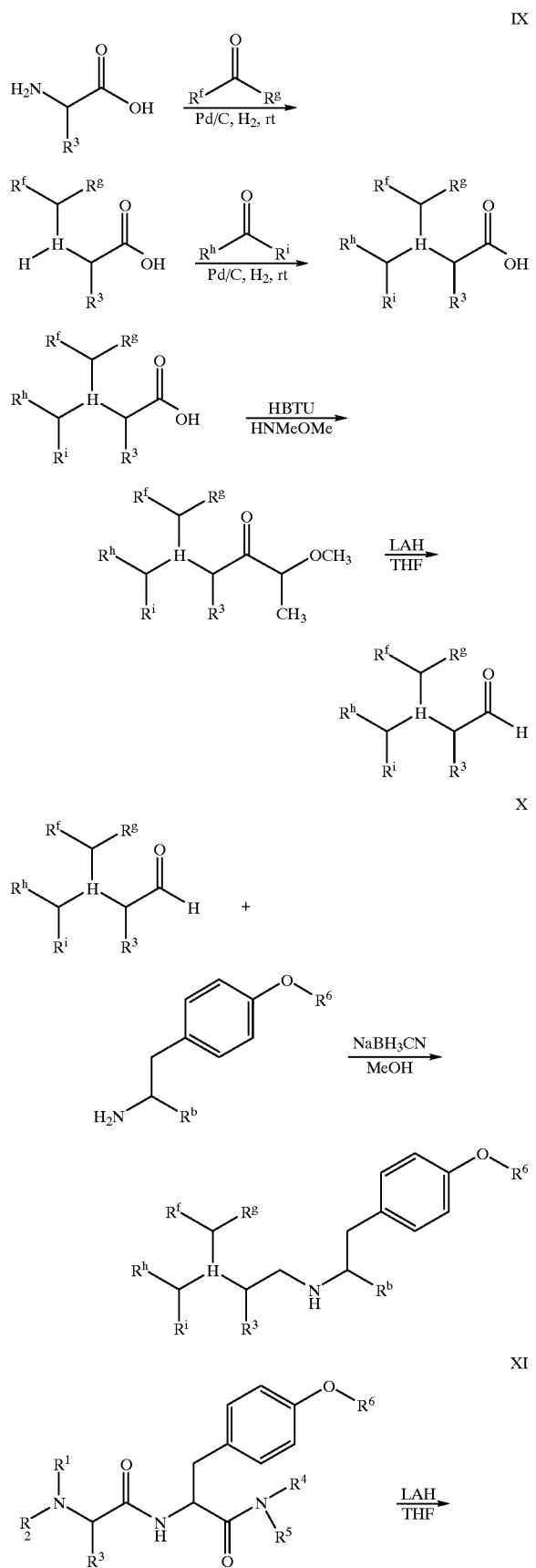

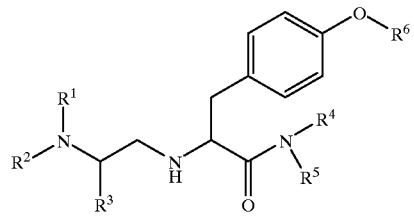

wherein $R^a$–$R^g$ are any chemical moiety consistent with the definitions of $R^1$–$R^7$.

The compounds of the invention are also useful research tools for studying the biological, cellular effects of blocking N-type calcium channels.

The invention further comprises a pharmaceutical composition for the treatment of illnesses induced by uncontrolled high concentrations of calcium in neurons, which composition comprises a compound of Formula I as defined above or, a pharmaceutically acceptable salt, solvent or pro-drug thereof, in an amount effective in the treatment of said illnesses, and a pharmaceutically acceptable carrier. The invention also comprises a pharmaceutical composition for the treatment of afflictions associated with increased calcium ion uptake through N-type calcium channels, including such systemic effects as stroke, pain, cerebral ischemia, head trauma, and epilepsy, which comprises a compound of Formula I as defined above in an amount effective in the treatment of said disorders, and a pharmaceutically acceptable carrier. Preferred compositions of the invention are those containing preferred compounds of Formula I as described above. The compounds will be administered to mammals at the rate of about 0.01 to about 200 mg/kg. Typical daily doses will be about 5 to about 500 mg per patient.

The term "pro-drug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The invention further relates to a method for the treatment of illnesses induced by uncontrolled high concentrations of calcium in neurons by administering to a subject in need of such treatment a compound of Formula I as defined above in an amount effective in such treatment, and a method for the treatment of stroke, pain, cerebral ischemia, head trauma, and epilepsy utilizing a compound of Formula I as defined above in an amount effective in such treatment. Preferred methods of the invention are those administering a preferred compound of the Formula I as described above.

The compounds of the present invention may be administered to a patient either alone or as part of a pharmaceutical composition. The compositions may be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin bentonite, and (i) lubricants, as for example, talc, calcium stearate, magnesium stearate, solid polyethylene glycols, sodium lauryl sulfate, or mixtures thereof. In case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils (in particular, cottonseed oil, groundnut oil, corn germ oil, olive oil, castor oil, and sesame oil), glycerol, tetrahydrofurfuryl alcohol, polyethyleneglycols and fatty acid esters of sorbitan or mixtures of these substances, and the like.

Besides such inert diluents, the composition can also include adjuvants such as wetting agents, emulsifying and suspending agents, sweetening agents, flavoring agents, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or intravaginal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active compound.

Dosage forms for topical administration of a compound of this invention include ointments, powders, sprays, and inhalants. The active component is admixed under sterile conditions with physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and pro-drugs" as used herein refers to those carboxylate salts, amino acid addition salts, esters, amides, and pro-drugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium, and the like, as well as nontoxic ammonium, quaternary ammonium, and amine cations, including, but not limited to, ammonium, tetramethylammonium, tetraethylammonium, methylamine, dimethylamine, trimethylamine, ethylamine, triethylamine, and the like. See, for example, Berge S. M., et al., "Pharmaceutical Salts," *J. Pharm. Sci.,* 1977;66:1–19, which is incorporated herein by reference.

Those skilled in the art are easily able to identify patients having a stroke or at risk of having a stroke, cerebral ischemia, head trauma, or epilepsy. For example, patients who are at risk of having a stroke include, but are not limited to, patients having hypertension or undergoing major surgery.

The invention will be described in greater detail in conjunction with the following specific examples. These examples are provided for illustrative purposes only and are

EXAMPLE 1

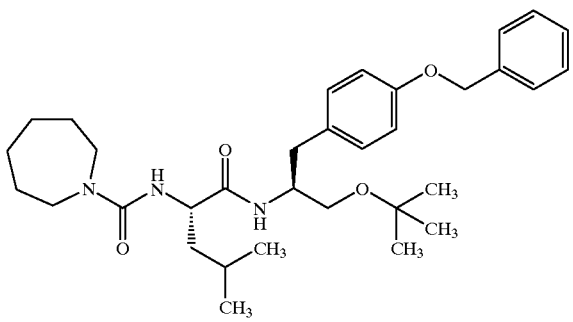

[S-(R*,R*)]-Azepane-1-carboxylic acid {1-[2-(4-benzyloxy-phenyl)-1-tert-butoxymethyl-ethylcarbamoyl]-3-methyl-butyl}-amide Step A:

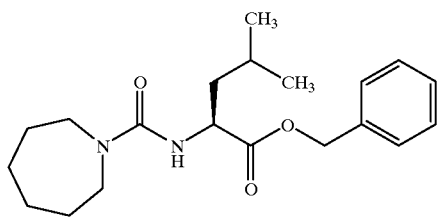

(S)-2-[Azepane-1-carbonyl)-amino]-
4-methyl-pentanoic acid benzyl ester

A solution of triphosgene (15.7 g, 52.9 mmol) in CH$_2$Cl$_2$ (600 mL) was cooled to −10° C. under a nitrogen atmosphere. The solution was treated dropwise with a solution of (S)-2-amino-4-methyl-pentanoic acid benzyl ester (28.1 g, 0.127 mol) and pyridine (26 mL, 0.32 mol) in 150 mL of CH$_2$Cl$_2$. The resulting solution was stirred at −10° C. for 90 minutes and then treated with a solution of hexamethyleneimine (22 mL, 0.38 mmol) in 75 mL of CH$_2$Cl$_2$. The resulting solution was stirred for 48 hours at room temperature. The reaction mixture was concentrated, and the residue was dissolved in ether and washed with 1N HCl solution, water, and saturated aqueous CuSO$_4$ solution. The organic layer was dried (Mg$_2$SO$_4$), treated with activated charcoal, and filtered. The filtrate was concentrated to approximately ½ volume and treated with hexane. The resulting suspension was stored overnight at −10° C. The solid was collected by filtration, washed with hexane, and dried under vacuum to give (S)-2-[(azepane-1-carbonyl)-amino]-4-methyl-pentanoic acid benzyl ester as a white solid (38.6 g, 88%); mp 87–88° C.

APCI-MS m/z 347 (MH$^+$).

Step B:

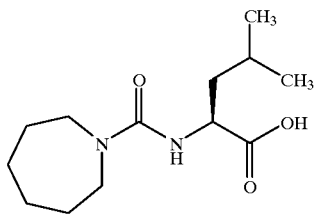

(S)-2-[Azepane-1-carbonyl)-amino]-4-methyl-pentanoic acid

A solution of (S)-2-[(azepane-1-carbonyl)-amino]-4-methyl-pentanoic acid benzyl ester (38.5 g, 111 mmol) in 600 mL of THF was hydrogenated at 50 psi over 20% Pd/C (2.00 g) for 17 minutes. The reaction mixture was filtered through celite and concentrated to dryness. The residue was heated in 50 mL of hexane. The resulting suspension was cooled, and the solid was collected by filtration and washed with hexane. The solid was dried at room temperature under vacuum to give (S)-2-[(azepane-1-carbonyl)-amino]-4-methyl-pentanoic acid as a white solid (26.6 g, 93%); mp 88–89° C.

Microanalysis for C$_{13}$H$_{24}$N$_2$O$_3$: Calculated: C, 60.91; H, 9.44; N, 10.93. Found: C, 60.99; H, 9.46; N, 10.85.

Step C:

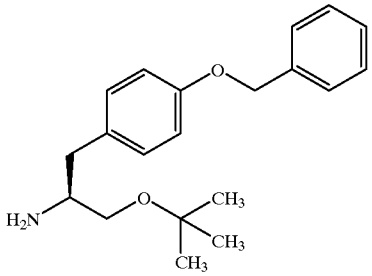

(S)-1-[4-Benzyloxy-benzyl)-2-tert-butoxy-ethylamine

A mixture of 2.573 g (10 mmol) (S)-β-amino-4-(phenylmethoxy)benzenepropanol (Advanced Chemtech, Louisville, Ky. 40218), 50 mL 2-methylpropene, 2 mL concentrated sulfuric acid, and 50 mL 1,4-dioxane were shaken in a glass pressure vessel at 25° C. for 62 hours. The milky-white suspension was poured into a rapidly stirred mixture containing 3.6 g 85% KOH, 75 mL ice-water, and 50 mL diethyl ether. After layers separated, the aqueous phase was extracted with two 50 mL portions of ethyl acetate. The combined extracts were washed with 100 mL brine, dried over anhydrous sodium sulfate, and concentrated in vacuo giving 288 mg of a pale amber oil which was purified by column chromatography (SiO$_2$) with 12:1 chloroform:methanol to give 131 mg (4%) of (S)-1-(4-benzyloxy-benzyl)-2-tert-butoxy-ethylamine as a clear, colorless oil, that was used directly in the next reaction.

Step D:

A 3° C. solution of 106 mg (0.41 mmol) (S)-2-[(azepane-1-carbonyl)amino]-4-methyl-pentanoic acid (Example 1, Step B) and 0.137 mL (0.41 mmol) 4-methylmorpholine in 2 mL N,N-dimethylformamide was treated with 165 mg (0.44 mmol) O-benzotriazol-1-yl-N,N,N',N'-bis(tetramethylene)uronium hexafluorophosphate (Novabiochem, La Jolla, Calif.), and stirred for 30 minutes, at which time a solution of (S)-1-(4-benzyloxy-benzyl)-2-tert-butoxy-ethylamine in 3 mL dimethylformamide was added and the mixture stirred at 3° C. for 40 minutes. The clear solution was poured into 15 mL diethyl ether and washed successively with 15 mL of each of the following: 5% aqueous HCl, brine, saturated aqueous NaHCO₃, brine (twice) then dried over anhydrous magnesium sulfate. The solvent was removed in vacuo affording 180 mg of white solid, which was recrystallized from hexane to give 116 mg (51%) of the title compound as a white solid; mp 98–99° C.

APCI-MS: m/z 552.0 [MH$^+$].

EXAMPLE 2

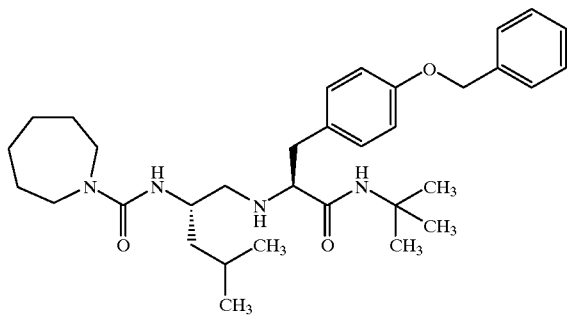

[S-(R*,R*)]Azepane-1-carboxylic acid (1-{[2-(4-benzyloxy-phenyl)-1-tert-butylcarbamoyl-ethylamino]-methyl}-3-methyl-butyl)-amide dihydrochloride salt Step A:

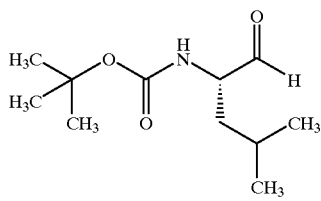

N-tert-Butoxycarbonyl-L-leucinal

N-tert-Butoxycarbonyl-L-leucinal was synthesized according to the procedure published Goet, et al., Org. Syn., 1988;67:69.

Step B:

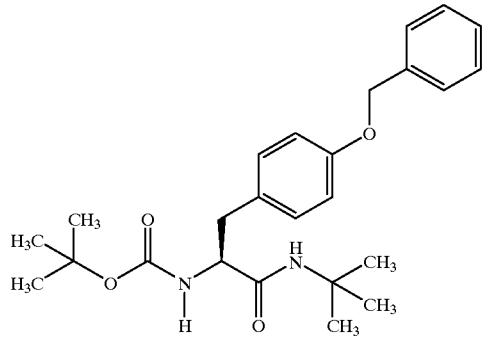

(S(-[2-[(1,1-Dimethylethyl)amino]-2-oxo-1-(phenylmethyl)ethyl]-carbamic acid 1,1-dimethylethyl ester A solution of N-(tert-butyloxycarbonyl)-O-benzyl-L-tyrosine (Bachem, 2.00 g, 5.38 mmol) in 20 mL of DMF was cooled to 0° C. and treated with iPr NEt (1.5 mL) followed by O-benzotriazol-1-yl-N,N,N',N'-bis(tetramethylene)-uronium hexafluoro phosphate (2.04 g, 5.38 mmol, Novabiochem, La Jolla, Calif.). The resulting suspension was stirred for 30 minutes at 0° C. and then treated with tert-butylamine (0.48 g, 6.56 mmol). The reaction mixture was stirred for 1 hour at 0° C. and warmed to room temperature. The reaction mixture was poured into Et O and washed sequentially with saturated aqueous NaHCO₃ solution, and saturated aqueous NaCl solution. The organic phase was dried (MgSO₄), filtered, and concentrated. The crude residue was purified by chromatography (silica gel, 3:1 heptane/ethyl acetate) to give (S)-[2-[(1,1-dimethylethyl)amino]-2-oxo-1-(phenylmethyl)ethyl]-carbamic acid 1,1-dimethylethyl ester (2.65 g).

MS (CI) 427 (MH).

Step C:

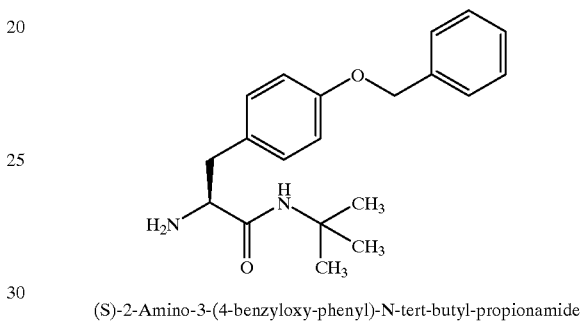

(S)-2-Amino-3-(4-benzyloxy-phenyl)-N-tert-butyl-propionamide

A solution of (S)-[2-(4-benzyloxy-phenyl)-1-tert-butylcarbamoyl-ethyl]-carbamic acid tert-butyl ester (6.0 g, 14.1 mmol, Example 2, Step B) in CH₂Cl₂ (28 mL) was treated with trifluoroacetic acid (28 mL). The resulting solution was stirred for 20 minutes and then concentrated. The residue was diluted with EtOAc (300 mL), washed with saturated bicarbonate solution (2×300 mL) and brine (300 mL), dried over Na₂SO₄, and concentrated to give 4.2 g (91%) of (S)-2-amino-3-(4-benzyloxy-phenyl)-N-tert-butyl-propionamide.

MS: 328 (M$^{+1}$ for $C_{20}H_{26}N_2O_3$).

TLC: Silica gel, R 0.43 (10% MeOH/CHCl).

Step D:

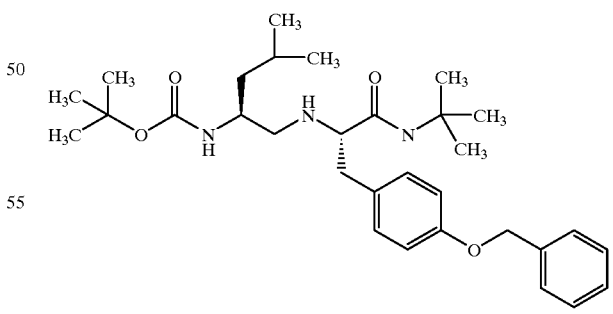

[S-(R*,S*)]-(1-{[2-(4-Benzyloxy-phenyl)-1-tert-butylcarbamoyl-ethyl-amino]-methyl}-3-methyl-butyl)-carbamic acid tert-butyl ester A solution consisting of 1.00 g (4.64 mmol) N-tert-butoxycarbonyl-L-leucinal and 1.52 g (4.64 mmol) 2-amino-3-(4-benzyloxy-phenyl)-N-tert-butyl-propionamide (Example 2, Step C) in 20 mL methanol containing 1% acetic acid was stirred at 25° C. for 20 minutes, at which time a solution of 0.614 g (9.29 mmol) sodium cyanotrihydridoborate (Aldrich, Milwaukee, Wis.) in 12 mL methanol was added and the resulting mixture stirred for 24 hours. The reaction was quenched by the addition of 3 M HCl in 3 mL increments until the vigorous bubbling subsided. The mixture was neutralized with saturated NaHCO$_3$ solution then extracted with three 50 mL portions of ethyl acetate. The combined extracts were washed with 100 mL brine, dried over anhydrous sodium sulphate, and evaporated at reduced pressure to give a clear, colorless oil which was chromatographed on a silica gel column using 30% to 40% ethyl acetate:hexane to give 735 mg (30%) of [S-(R*,S*)]-(1-{[2-(4-benzyloxy-phenyl)-1-tert-butylcarbamoyl-ethylamino]-methyl}-3-methyl-butyl)-carbamic acid tert-butyl ester as a clear foam.

APCI-MS: m/z 526.3 [MH$^+$].

Microanalysis for $C_{31}H_{47}N_3O_4 \cdot 0.25\ H_2O$: Calculated: C, 70.22; H, 9.03; N, 7.92. Found: C, 70.27; H, 9.09; N, 7.78.

Step E:

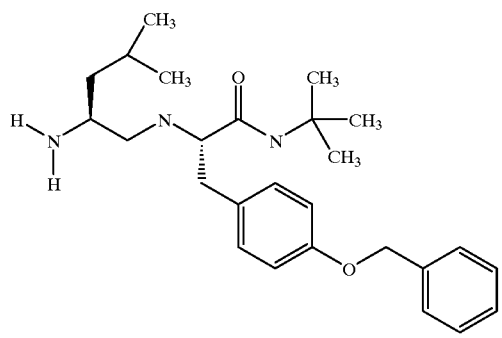

(S,S)-2-(2-Amino-4-methyl-pentylamino)-3-(4-benzyloxy-phenyl)-N-tert butyl-propionamide A solution of 850 mg (1.6 mmol) (1-{[2-(4-benzyloxy-phenyl)-1-tert-butylcarbamoyl-ethylamino]-methyl}-3-methyl-butyl)-carbamic acid tert-butyl ester in 6 mL dichloromethane was treated with 2 mL 2,2,2-triflouroacetic acid and the resulting solution stirred 1 hour at 25° C. The mixture was concentrated at reduced pressure to a viscous amber oil to which was dissolved in 8 mL diethyl ether, and treated with 3 mL of diethyl ether which had been saturated with hydrogen chloride gas. The solvent was removed under reduced pressure, and the pale yellow oil thus obtained ((S,S)-2-(2-amino-4-methyl-pentylamino)-3-(4-benzyloxy-phenyl)-N-tert-butyl-propionamide) was used directly in the next reaction.

Step F:

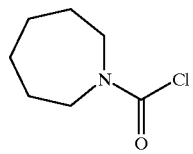

Azepane-1-carbonyl chloride

Azepane-1-carbonyl chloride was made according to the procedure reported in *Tetrahedron Lett.*, 1994;35:839.

Step G

A solution of 746 mg (1.6 mmol) 2-(2-amino-4-methyl-pentylamino)-3-(4-benzyloxy-phenyl)-N-tert-butyl-propionamide, 0.408 mL (3.1 mmol) hexahydroazepinyl carbamoyl chloride, 20 mg (0.16 mmol) 4-dimethylaminopyridine (Aldrich, Milwaukee, Wis.), 0.818 mL (4.7 mmol) N,N-diisopropylethylamine (Aldrich, Milwaukee, Wis.), in 10 mL of benzene was heated under reflux for 16 hours, cooled to 25° C. and filtered, and the solids washed with benzene. The filtrate was concentrated under reduced pressure, and the residue thus obtained was dissolved in 100 mL ethyl acetate, and washed with 100 mL each saturated NaHCO$_3$ solution and brine, dried over anhydrous magnesium sulfate, then concentrated under reduced pressure to give a pale amber oil that was purified by column chromatography on silica gel with 1:1 ethyl acetate:chloroform as eluant. The clear, colorless oil obtained was dissolved in 10 mL diethyl ether, and treated with diethyl ether that had been saturated with hydrogen chloride gas. The precipitate that formed was collected by filtration, and the solids washed with ethyl acetate and dried. The title compound was obtained as 440 mg off-white solid (77%); mp 51–57° C.

APCI-MS: m/z 551.4 [MH$^+$].

EXAMPLE 3

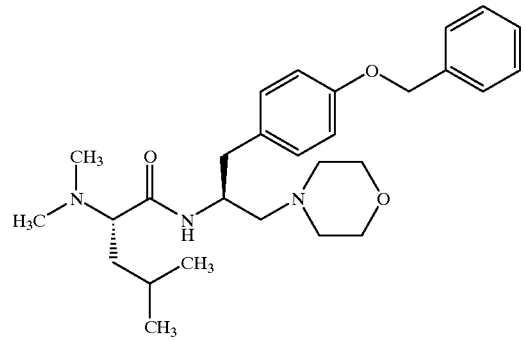

[S-(R*,R*)]-2-Dimethylamino-4-methyl-pentanoic acid [2-(4-benzyloxy-phenyl)-1-morpholin-4-ylmethyl-ethyl]-amide Step A:

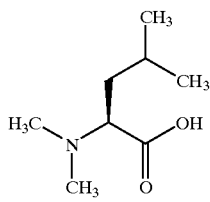

(S)-2-Dimethylamino-4-methyl-pentanoic acid (S)-2-Dimethylamino-4-methyl-pentanoic acid was synthesized according to the procedure described in *J. Chem. Soc.*, 1950:1342–1345.

Step B:

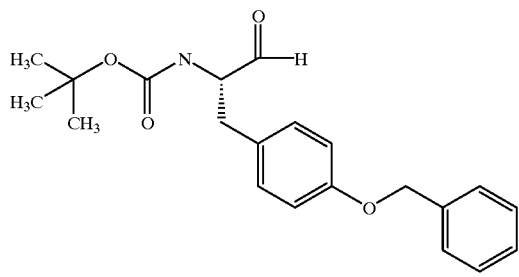

N-tert-Butoxycarbonyl-O-benzyl-L-tyrosinal

N-tert-Butoxycarbonyl-O-benzyl-L-tyrosinal was synthesized according to the procedure published in Thompson, et al., *Tetrahedron Lett.*, 1990;31:6819–6822.

Step C:

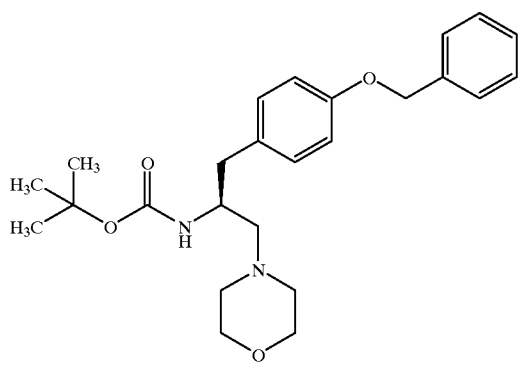

[2-(4-Benzyloxy-phenyl)-1-morpholin-4-ylmethyl-ethyl]-carbamic acid tert-butyl ester A solution consisting of 2.86 g (8 mmol) N-tert-butoxycarbonyl-O-benzyl-L-tyrosinal and 0.701 mL (8 mmol) morpholine (Aldrich, Milwaukee, Wis.) in 36 mL methanol containing 1% acetic acid was stirred at 25° C. for 20 minutes, at which time a solution of 1.06 g (16 mmol) sodium cyanotrihydridoborate (Aldrich, Milwaukee, Wis.) in 12 mL methanol was added and the resulting mixture stirred for 24 hours. The reaction was quenched by the addition of 3 M HCl in 3 mL increments until the vigorous bubbling subsided. The mixture was neutralized with saturated $NaHCO_3$ solution then extracted with three 100 mL portions of ethyl acetate. The combined extracts were washed with 100 mL brine, dried over anhydrous sodium sulphate, and evaporated at reduced pressure to give a clear, colorless oil which was chromatographed on a silica gel column using ethyl acetate:hexane, 1:1 as eluant. The A white, waxy solid was recrystallized from 2,2,4-trimethylpentane to give 1.53 g (45%) of [2-(4-benzyloxy-phenyl)-1-morpholin-4-ylmethyl-ethyl]-carbamic acid tert-butyl ester as soft white crystals; mp 98–99° C.

APCI-MS m/z 427.2 [MH$^+$].

Microanalysis for $C_{34}H_{47}N_3O.0.25H_2O$: Calculated: C, 78.80; H, 9.24; N, 8.11. Found: C, 78.64; H, 9.56; N, 7.95.

Step D:

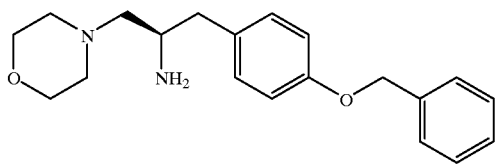

(S)-2-(4-Benzyloxy-phenyl)-1-morpholin-4-ylmethyl-ethylamine

A solution of 1.41 g (3.3 mmol) [2-(4-benzyloxy-phenyl)-1-morpholin-4-ylmethyl-ethyl]-carbamic acid tert-butyl ester in 5 mL dichloromethane was treated with 1.5 mL 2,2,2-triflouroacetic acid and the resulting solution stirred 16 hours at 25° C. The mixture was concentrated at reduced pressure to a viscous amber oil to which was added 50 mL saturated aqueous sodium bicarbonate solution and the resulting mixture extracted with three 50 mL portions of ethyl acetate. The combined extracts were washed with 100 mL brine, dried over anhydrous sodium sulfate and concentrated at reduced pressure affording a soft solid, that was recrystallized from 2,2,4-trimethylpentane containing about 5% ethyl acetate to afford 804 mg (77%) of (S)-2-(4-benzyloxy-phenyl)-1-morpholin-4-ylmethyl-ethylamine as light tan crystals; mp 180–182° C.

MS: m/z 327.2 [MH$^+$].

Step E (S)-2-Dimethylamino-4-methyl-pentanoic acid (55.3 mg, 0.347 mmol) was dissolved in dry DMF (3 mL) under nitrogen atmosphere and cooled to 0° C. in an ice-water bath. To this solution were added in succession N,N-diisopropylethylamine (0.180 mL, 1.04 mmol) and solid O-benzotriazol-1-yl-N,N,N',N'tetramethyluronium hexafluorophosphate (132 mg, 0.347 mmol, Novabiochem, La Jolla, Calif.). The resulting reaction mixture was stirred at that temperature for 30 minutes, (S)-2-(4-benzyloxy-phenyl)-1-morpholin-4-ylmethyl-ethylamine (153 g, 0.347 mmol, Example 3, Step D) was then added. After an additional 60 minutes stirring at 0° C., the reaction mixture was mixed with 60 mL of diethyl ether, and the resulting mixture was successively washed with saturated aqueous $NaHCO_3$ solution and brine and then dried over $Na_2SO_4$. The solution was concentrated in vacuo, an oil was obtained. The crude product was purified by chromatography (silica gel, 10% methanol in chloroform) to give the title compound as a white solid (90 mg, 55%); mp 113–114° C.

APCI-MS: m/z 468.4 (MH$^+$).

EXAMPLE 4

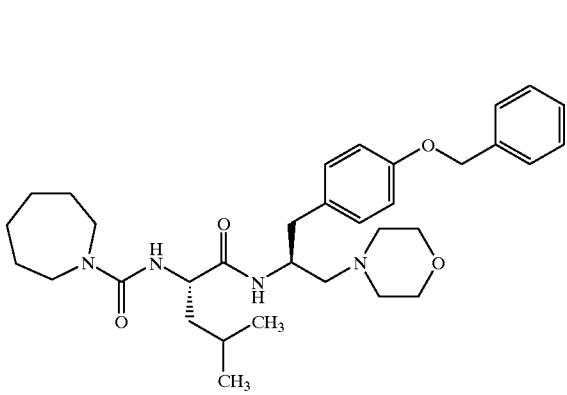

[S-(R*,R*)]-Azepane-1-carboxylic acid{1-[2-(4-benzyloxy-phenyl)-1-morpholin-4-ylmethyl-ethylcarbamoyl]-3-methyl-butyl}-amide A solution of 87 mg (0.34 mmol) of (S)-2-[(azepane-1-carbonyl)-amino]-4-methyl-pentanoic acid (Example 1, Step B) and 0.131 mL (1.2 mmol) 4-methylmorpholine was stirred at 25° C. for 30 minutes, after which 136 mg (0.36 mmol) O-benzotriazol-1-yl-N,N,N',N'-bis(tetramethylene) uronium hexafluorophosphate in 4 mL dry DMF was added. The resulting solution was cooled in an ice-bath and 150 mg (0.34 mmol) 2-(4-benzyloxy-phenyl)-1-morpholin-4-ylmethyl-ethylamine (Example 3, Step D) was added. The resulting solution was warmed to 25° C. and stirred for 30 minutes. The mixture was then poured into 35 mL diethyl ether, and washed sequentially with 25 mL each of 2.5% aqueous HCl solution, brine, saturated aqueous sodium bicarbonate solution, and finally twice with brine. The mixture was then dried over anhydrous sodium sulfate and concentrated at reduced pressure to give an amber oil that was purified by preparative thin-layer chromatography on a 1000 μm silica gel plate with 50:50:1 ethyl acetate:hexane:methanol as eluant to give 46 mg (24%) of the title compound as a pale amber glass.

APCI-MS: m/z 565.5 [MH+].

Microanalysis for $C_{33}H_{48}N_4O_4 \cdot 0.25$EtOAc: Calculated: C, 69.59; H, 8.59; N, 9.55. Found: C, 69.70; H 8.67; N, 9.39.

EXAMPLE 5

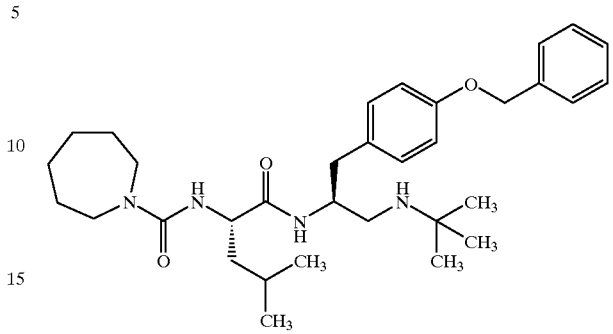

[S-(R*,R*)]-Azepane-1-carboxylic acid{1-[2-(4-benzyloxy-phenyl)-1-(tert-butylamino-methyl)-ethyl-ethylcarbamoyl]-3-methyl-butyl}-amide trifloroacetate salt (1:1)

Step A:

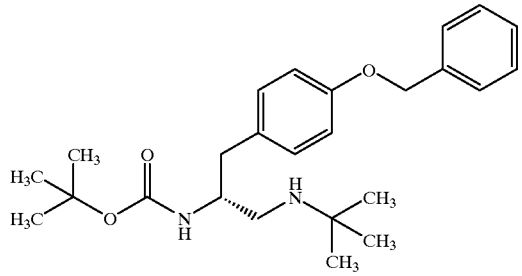

(S)-[2-(4-Benzyloxy-phenyl)-1-(tert-butylamino-methyl)-ethyl]-carbamic acid tert-butyl ester A solution consisting of 2.86 g (8 mmol) N-tert-butoxycarbonyl-O-benzyl-L-tyrosinal (Example 4, Step A) and 0.846 mL (8 mmol) tert-butyl amine (Aldrich, Milwaukee, Wis.) in 36 mL methanol containing 1% acetic acid was stirred at 25° C. for 20 minutes, at which time a solution of 1.06 g (16 mmol) sodium cyanotrihydridoborate (Aldrich, Milwaukee, Wis.) in 12 mL methanol was added and the resulting mixture stirred for 48 hours. The reaction was quenched by the addition of 3 M HCl in 3 mL increments until the vigorous bubbling subsided. The mixture was neutralized with saturated $NaHCO_3$ solution then extracted with three 100 mL portions of ethyl acetate. The combined extracts were washed with 100 mL brine, dried over anhydrous sodium sulphate and evaporated at reduced pressure to give a pale amber oil which was chromatographed on a silica gel column using 1% to 2% methanol in ethyl acetate as eluant to give 604 mg (18%) of the title compound as waxy white crystals; mp 77–79° C.

APCI-MS m/z 413.2 [MH+].

Step B:

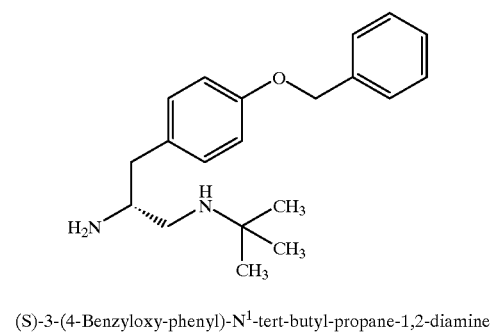

(S)-3-(4-Benzyloxy-phenyl)-N¹-tert-butyl-propane-1,2-diamine

A solution of 1.41 g (3.3 mmol) [2-(4-benzyloxy-phenyl)-1-morpholin-4-ylmethyl-ethyl]-carbamic acid tert-butyl ester in 5 mL dichloromethane was treated with 1.5 mL 2,2,2-triflouroacetic acid and the resulting solution stirred 16 hours at 25° C. The mixture was concentrated at reduced pressure to a viscous amber oil to which was added 50 mL saturated aqueous sodium bicarbonate solution and the resulting mixture extracted with three 50 mL portions of ethyl acetate. The combined extracts were washed with 100 mL brine, dried over anhydrous sodium sulfate and concentrated at reduced pressure affording a soft solid, that was recrystallized from 2,2,4-trimethylpentane containing about 5% ethyl acetate to afford 804 mg (77%) of the title compound as light tan crystals; mp 180–182° C.

APCI-MS m/z 382.2 [MH+].

Step C

A solution of 200 mg (0.79 mmol) of (S)-2-[(azepane-1-carbonyl)-amino]-4-methyl-pentanoic acid (Example 1, Step B) and 0.260 mL (2.4 mmol) 4-methylmorpholine in 4 mL DMF was stirred at 25° C. for 0.5 hour, and 298 mg (0.79 mmol) O-benzotriazol-1-yl-N,N,N',N'-bis(tetramethylene)uronium hexafluorophosphate was added, and the resulting solution cooled in an ice-bath and stirred 30 minutes, and 236 mg (0.79 mmol) of [2-(4-benzyloxy-phenyl)-1-(tert-butylamino-methyl)-ethylamine was added and the resulting solution warmed to 25° C. and stirred 30 minutes. The mixture was poured into 50 mL diethyl ether, and washed with 55 mL saturated aqueous sodium bicarbonate solution, and finally twice with 75 mL brine, and dried over anhydrous sodium sulfate and concentrated at reduced pressure to give a pale amber oil that was purified by column chromatography on silica gel with 3% methanol in chloroform as eluant to give 117 mg (27%) of the title compound as a white foam.

APCI-MS m/z 565.5 [MH+].

Microanalysis for $C_{33}H_{50}N_4O_3 \cdot TFA \cdot 0.5\ H_2O$: Calculated: C, 62.39; H, 7.78; N, 8.31; $H_2O$, 1.34. Found: C, 62.45; H 8.17; N, 8.58; $H_2O$, 1.57.

EXAMPLE 6

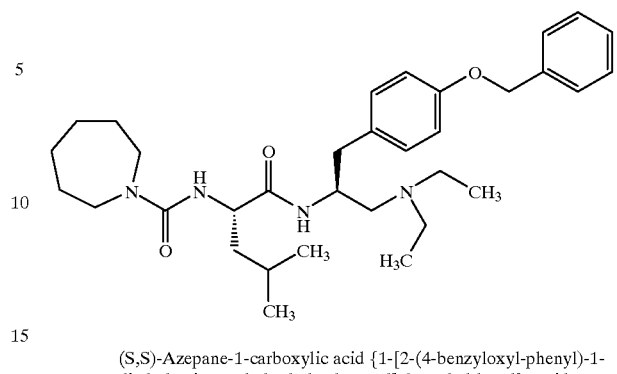

(S,S)-Azepane-1-carboxylic acid {1-[2-(4-benzyloxyl-phenyl)-1-diethylaminomethyl-ethylcarbamoyl]-3-methyl-butyl}-amide Step A:

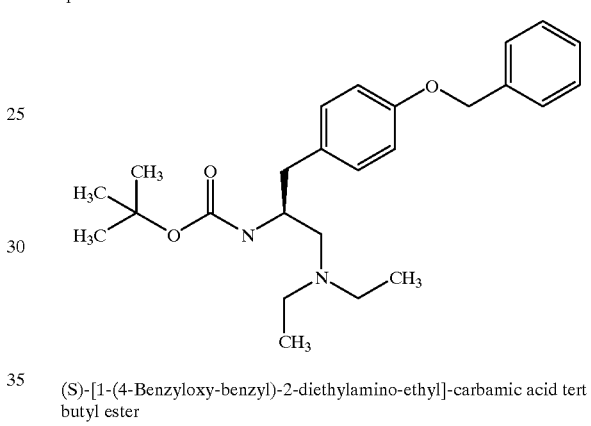

(S)-[1-(4-Benzyloxy-benzyl)-2-diethylamino-ethyl]-carbamic acid tert butyl ester A solution consisting of 2.86 g (8 mmol) N-tert-butoxycarbonyl-O-benzyl-L-tyrosinal (Example 3, Step B) and 0.832 mL (8 mmol) diethyl amine in 36 mL methanol containing 1% acetic acid was stirred at 25° C. for 20 minutes, at which time a solution of 1.06 g (16 mmol) sodium cyanotrihydridoborate (Aldrich, Milwaukee, Wis.) in 12 mL methanol was added and the resulting mixture stirred for 48 hours. The reaction was quenched by the addition of 3 M HCl in 3 mL increments until the vigorous bubbling subsided. The mixture was neutralized with saturated $NaHCO_3$ solution then extracted with three 100 mL portions of ethyl acetate. The combined extracts were washed with 100 mL brine, dried over anhydrous sodium sulphate and evaporated at reduced pressure to give an amber oil which was chromatographed on a silica gel column using 50:50:1 ethyl acetate:hexane:methanol as eluant to give 236 mg (7%) of (S)-[1-(4-benzyloxy-benzyl)-2-diethylamino-ethyl]-carbamic acid tert-butyl ester as a clear, colorless oil.

APCI-MS: m/z 413.2 [MH+].

¹H NMR (CDCl₃): 7.40–7.28 (5H, m), 7.08 (2H, d, J=8.5 Hz), 6.86 (2H, d, J=8.5 Hz), 5.00 (2H, s), 3.77 (1H, bs), 2.77–2.37 (7H, m), 1.38 (9H, s), 0.96 (6H, bs).

Step B:

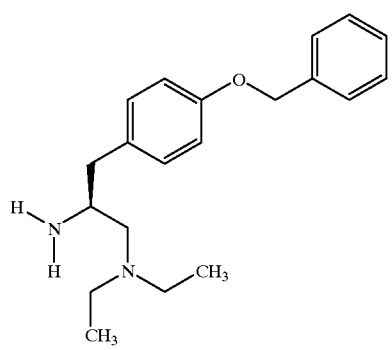

(S)-3-(4-Benzyloxy-phenyl)-N$^1$,N$^1$-diethyl-propane-1,2-diamine

A solution of 171 mg (0.4 mmol) [2-(4-benzyloxy-phenyl)-1-(diethylamino-methyl)-ethyl]-carbamic acid tert-butyl ester in 2 mL dichloromethane was treated with 0.5 mL 2,2,2-triflouroacetic acid and the resulting solution stirred 3 hours at 25° C. The mixture was concentrated at reduced pressure to a viscous amber oil to which was added 30 mL saturated aqueous sodium bicarbonate solution and the resulting mixture extracted with three 20 mL portions of ethyl acetate. The combined extracts were washed with two 50 mL portions of brine, dried over anhydrous sodium sulfate, and concentrated at reduced pressure and the residue purified by column chromatography using ethyl acetate containing 1% methanol as eluent. There was obtained 112 mg (90%) of (S)-3-(4-benzyloxy-phenyl)-N$^1$,N$^1$-diethyl-propane-1,2-diamine as a clear, colorless oil.

APCI-MS: m/z 313.2 [MH$^+$].

$^1$H NMR (CDCl$_3$): 7.37–7.25 (5H, m), 7.07 (2H, d, J=8.06 Hz), 6.85 (2H, d, J=7.8 Hz), 4.98 (2H, s), 3.05 (1H, bs), 2.67–2.24 (6H, m), 0.96 (6H, t).

Step C

A solution of 53 mg (0.20 mmol) of (S)-2-[(azepane-1-carbonyl)-amino]-4-methyl-pentanoic acid (Example 1, Step B) and 0.079 mL (7.2 mmol) 4-methylmorpholine in 4 mL DMF was stirred at 25° C. for 0.5 hour, and 82 mg (0.21 mmol) O-benzotriazol-1-yl-N,N,N',N'-bis(tetramethylene)uronium hexafluorophosphate was added. The resulting solution was cooled in an ice-bath and stirred 30 minutes, after which 64 mg (0.20 mmol) of (S)-3-(4-benzyloxy-phenyl)-N$^1$,N$^1$-diethyl-propane-1,2-diamine in 2 mL DMF was added. The resulting solution was warmed to 25° C. and stirred for 30 minutes. The mixture was then poured into 30 mL diethyl ether, and washed with 25 mL each of 5% HCl solution, brine, saturated aqueous sodium bicarbonate solution, and finally twice with brine. The mixture was dried over anhydrous sodium sulfate and concentrated at reduced pressure to give a clear, colorless oil that was purified by preparative thin-layer chromatography on a 500 μm silica gel plate using 50:50:1 ethyl acetate:hexane:methanol as eluant to give 21.2 mg (19%) of the title compound as a clear, colorless oil.

APCI-MS: m/z 551.5 [MH$^+$].

Microanalysis for C$_{33}$H$_{48}$N$_4$O$_3$·0.5 H$_2$O: Calculated: C, 70.81; H, 9.18; N, 10.01; H$_2$O, 1.61. Found: C, 70.64; H 8.97; N, 9.73; H$_2$O, 1.29.

EXAMPLE 7

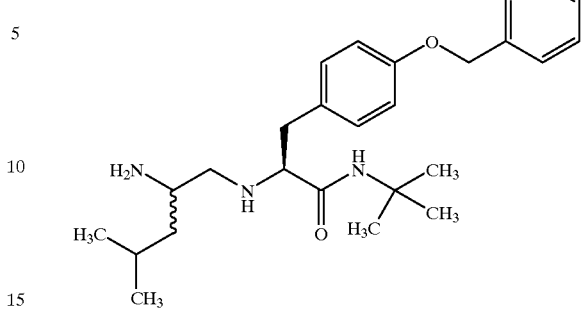

(S)-2-(2-Amino-4-methyl-pentylamino)-3-(4-benzyloxy-phenyl)-N-tert-butyl-propionamide dihydrochloride Step A:

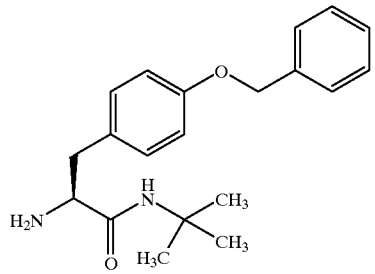

(S)-2-Amino-3-(4-benzyloxyl-phenyl)-N-tert-butyl-propionamide monohydrochloride

To a solution of (S)-2-amino-3-(4-benzyloxy-phenyl)-N-tert-butyl-propionamide (Example 2, Step C) in ether was added excess amount of ethereal HCl, solid formed was isolated via filtration, subsequent drying under vacuum gave title compound as a yellow solid.

Step B (1-{[2-(4-Benzyloxy-phenyl)-1-tert-butylcarbamoyl-ethylamino]-methyl}-3-methyl-butyl)-carbamic acid tert-butyl ester (S)-2-Amino-3-(4-benzyloxy-phenyl)-N-tert-butyl-propionamide monohydrochloride (1.68 g, 4.65 mmol, Example 7, Step A) and BOC-Leu-CHO ((tert-butoxy)-N-[1-(2-methylpropyl)-2-oxoethyl]carboxamide) (1.00 g, 4.65 mmol, Peninsula Laboratories, Belmont, Calif.) were mixed in CH$_2$Cl$_2$ (25 mL). After stirring at ambient temperature under nitrogen atmosphere for 30 minutes, the solution was cooled to 0° C. in an ice-water bath. To this solution was added sodium triacetoxyborohydride (1.50 g, 6.98 mmol). The resulting reaction mixture was stirred for, in succession, 30 minutes at 0° C. and 12 hours at ambient temperature. Twenty-five milliliters of saturated aqueous NaHCO$_3$ solution was added to the reaction mixture, and the resulting mixture was stirred for 5 minutes. The two layers were separated, and the aqueous layer was extracted with CH$_2$Cl$_2$ (2×30 mL). The combined organic solution was dried over Na$_2$SO$_4$. The solution was concentrated in vacuo affording a viscous oil. The reaction gave two diastereomers which were purified twice by column chromatography (eluant used in first column chromatography: 30% EtOAc-4% MeOH-66% hexanes; eluant used in second column chromatography: 100% acetonitrile). When the solvent system, 30% EtOAc-66% benzene-4% MeOH, was used as eluant. The two diastereomers gave different $R_f$ values on TLC (0.68 and 0.53). The compound with a $R_f$ value of 0.68 was isolated by preparative plate as a yellow oil (0.3 g) and used in used step.

Step C

To a solution of (1-{[2-(4-benzyloxy-phenyl)-1-tert-butylcarbamoyl-ethylamino]-methyl}-3-methyl-butyl)-carbamic acid tert-butyl ester (0.4 g, 0.76 mmol, Example 7, Step B) in $CH_2Cl_2$ (7.5 mL) was added trifluoroacetic acid (2.5 mL) at ambient temperature under nitrogen atmosphere. The resulting reaction mixture was stirred for 25 minutes, then concentrated in vacuo. The viscous oil obtained was dissolved in 40 mL of $CH_2Cl_2$ and successively washed with saturated aqueous $NaHCO_3$ solution (2×40 mL), brine (2×40 mL), and was dried over $Na_2SO_4$. The $CH_2Cl_2$ solution of free amine was concentrated in vacuo to afford the crude product as a viscous oil which was then dissolved in 10 mL of ethyl ether. To this solution was added saturated HCl solution in ethyl ether until no more white precipitate formed. Filtration and drying overnight under vacuum afforded 0.23 g (61%) of titled compound as a yellow solid; mp 228–230° C.

APCI-MS m/z 426.1 ($MH^+$).

EXAMPLE 8

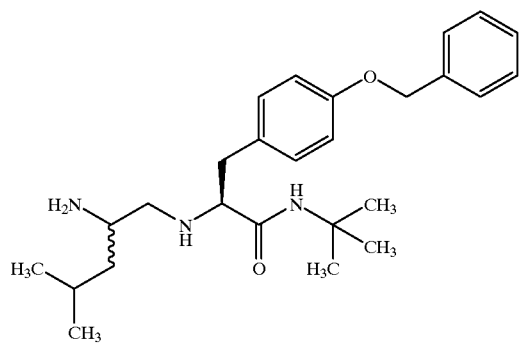

2-(2-Amino-4-methyl-pentylamino)-3-(4-benzyloxy-phenyl)-N-tert-butyl propionamide dihydrochloride Step A:

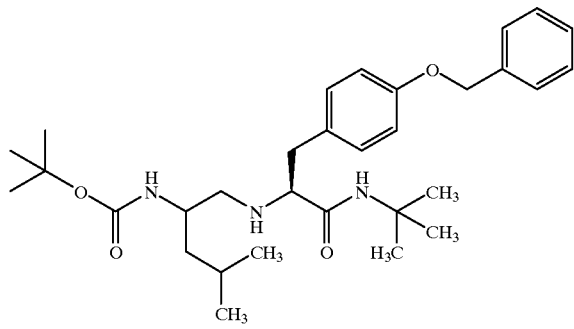

(1-{[2-4-Benzyloxy-phenyl)-1-tert-butylcarbamoyl-ethylamino]-methyl}-3-methyl-butyl)-carbamic acid tert-butyl ester (S)-2-Amino-3-(4-benzyloxy-phenyl)-N-tert-butyl-propionamide monohydrochloride (1.68 g, 4.65 mmol, Example 7, Step A) and BOC-Leu-CHO ((tert-butoxy)-N-[1-(2-methylpropyl)-2-oxoethyl]carboxamide) (1.00 g, 4.65 mmol, Peninsula Laboratories, Belmont, Calif.) were mixed in $CH_2Cl_2$ (25 mL). After stirring at ambient temperature under nitrogen atmosphere for 30 minutes, the solution was cooled to 0° C. in an ice-water bath. To this solution was added sodium triacetoxyborohydride (1.50 g, 6.98 mmol). The resulting reaction mixture was stirred for, in succession, 30 minutes at 0° C. and 12 hours at ambient temperature. Twenty-five milliliters of saturated aqueous $NaHCO_3$ solution was added to the reaction mixture, and the resulting mixture was stirred for 5 minutes. The 2 layers were separated, and the aqueous layer was extracted with $CH_2Cl_2$ (2×30 mL). The combined organic solution was dried over $Na_2SO_4$. The solution was concentrated in vacuo affording a viscous oil. The reaction gave two diastereomers which were purified twice by column chromatography (eluant used in first column chromatography: 30% EtOAc-4% MeOH-66% hexanes; eluant used in second column chromatography: 100% acetonitrile). When the solvent system, 30% EtOAC-66% benzene-4% MeOH, was used as eluant, The two diastereomers gave different $R_f$ values on TLC (0.68 and 0.53). The compound with a $R_f$ value of 0.53 was isolated by preparative plate as a yellow oil (0.27 g) and used in used step.

Step B

To a solution of (1-{[2-(4-benzyloxy-phenyl)-1-tert-butylcarbamoyl-ethylamino]-methyl}-3-methyl-butyl)-carbamic acid tert-butyl ester (0.4 g, 0.76 mmol, Example 8, Step A) in $CH_2Cl_2$ (7.5 mL) was added trifluoroacetic acid (2.5 mL) at ambient temperature under nitrogen atmosphere. The resulting reaction mixture was stirred for 25 minutes, then concentrated in vacuo. The viscous oil obtained was dissolved in 40 mL of $CH_2Cl_2$ and successively washed with saturated aqueous $NaHCO_3$ solution (2×40 mL), brine (2×40 mL), and was dried over $Na_2SO_4$. The $CH_2Cl_2$ solution of free amine was concentrated in vacuo to afford the crude product as a viscous oil which was then dissolved in 10 mL of ethyl ether. To this solution was added saturated HCl solution in ethyl ether until no more white precipitate formed. Filtration and drying overnight under vacuum afforded 0.15 g (59%) of titled compound as a yellow solid; mp 228–230° C.

APCI-MS m/z 426.1 ($MH^+$).

EXAMPLE 9

Biological Assays

Measurement of N-type $Ca^{2+}$ Channel Blocking Potencies of Compounds in IMR32 Cells Using the Fluorescent $Ca^{2+}$ Indicator Indo-1

IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 μM nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

The IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimicotic mixture (Gibco). At approximately 80% confluency, differentiation was induced by the addition of 1 mM dibutyryl cAMP and 2.5 μM bromodeoxyuridine to the medium. After 7 to 13 days of differentiation, cells were detached using 0.5 mM EDTA and loaded with 5 μM Indo-1 acetoxymethyl ester (Molecular Probes, Eugene, Oreg.) at 300° C. for 45 minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostated cuvette holder with stirring capabilities as well as with a computer-controlled pump that allowed for reagent addition during measurement. Instrument control and data collection was done by PTI's OSCAR software running on an IBM compatible computer. Different concentrations of the test compounds (60 μL in dimethyl sulfoxide) were added to 5.94 mL of assay buffer containing approximately $3\times10^6$ loaded cells, and 5 μM Nitrendipine (in 30 μL EtOH) to block L-type $Ca^{2+}$ channels. Samples were incubated for 10 minutes at 30° C. and then aliquoted into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 μL of stimulation solution (1M KCl, 68 mM $CaCl_2$) to the cuvette via the computer-controlled pump. Ratio of dual emission signals (400 nm/490 nm), which is proportional to intracellular $Ca^{2+}$ concentration, was plotted against time, and the difference between maximal response after stimulation and basal value (before stimulation) was determined. Values obtained in this way were plotted as a function of drug concentration. $IC_{50}$ values of test compounds were calculated by fitting a 4-parameter logistic function to the data using the least squares method.

The following are the results for the IMR32 and FLP150 assays:

TABLE 1

| Compound of Example No. | IMR32 $IC_{50}$ (μM) |
|---|---|
| 1 | 0.21 |
| 2 | 0.19 |
| 3 | 48% @ 10 μM |
|   | 6% @ 1 μM |
| 4 | 1.2 |
| 5 | 1.1 |
| 6 | 1.1 |
| 7 | 1.2 |
| 8 | 1 |

Audiogenic Seizure Model in DBA/2 Mice

Compounds of the present invention were dissolved in water using 10% (weight/volume) Emulphor (GAF Corp., Wayne, N.J.) surfactant. Substances were administered by intravenous injection into the retro-orbital venous sinus. All testing was performed 15 minutes or 45 minutes after drug injection. All the male mice, 3 to 4 weeks old, were obtained from Jackson Laboratories, Bar Harbour, Me. Immediately before anticonvulsant testing, mice were placed upon a wire mesh, 4 inches square suspended from a steel rod. The square was slowly inverted through 180 degrees, and the mice were observed for 30 seconds. Any mouse falling from the wire mesh was scored as ataxic.

Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 seconds) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds.

The incidence of all the seizure phases in the drug-treated and vehicle-treated mice was recorded, and the occurrence of tonic seizures were used for calculating anticonvulsant ED values by probit analysis. Mice were used only once for testing at each time and dose point.

Compound 2 was found to give 100% protection at 30 mg/kg at 15 minutes posttreatment time, and Compound 1 gave 80% protection at 30 mg/kg at 15 minutes posttreatment time.

TABLE 2

| Compound of Example No. Number | Dose (mg/kg, IV) | Time Post Treatment (minutes) | Number of Mice Protected from Tonic Convulsions* |
|---|---|---|---|
| 1 | 30 | 15 | 4/5 |
| 1 | 30 | 45 | 2/5 |
| 1 | 10 | 15 | 1/5 |
| 2 | 30 | 15 | 5/5 |
| 2 | 30 | 45 | 1/5 |
| 2 | 10 | 15 | 1/5 |
| 7 | 10 | 15 | 2/5 |
| 7 | 10 | 45 | 1/5 |
| 8 | 10 | 15 | 0/5 |
| 8 | 10 | 45 | 0/5 |

*Number of mice protected from tonic convulsions/Number of mice tested

What is claimed is:

1. A compound having structural Formula I:

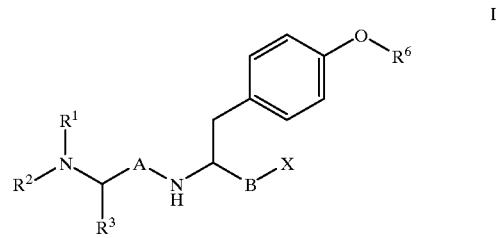

wherein $R^1$ is H or methyl, $R^2$ is H, azepanylcarbonyl, $C_1$–$C_7$ alkyl, —$(CH_2)_n$-phenyl, wherein the phenyl is unsubstituted or substituted with $C_1$–$C_4$-alkyl, $C_1$–$C_4$ alkoxy, or halo, $R^3$ is $C_1$–$C_5$ alkyl, X is —$NR^4R^5$ or —$OR^7$, $R^4$ and $R^5$ are independently H, $C_1$–$C_5$ alkyl, or $R^4$ and $R^5$ together with the nitrogen to which they are both bound form:

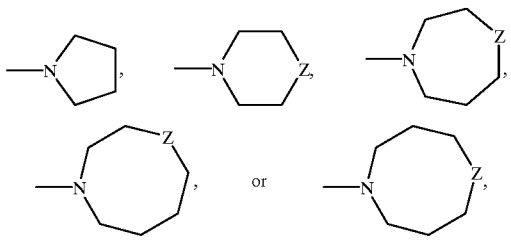

$R^6$ is —$(CH_2)_n$-phenyl, wherein the phenyl is unsubstituted or substituted with $C_1$–$C_4$ alkyl, $C_1$–$C_4$ alkoxy, or halo, A and B are independently —CO— or —$CH_2$—, provided that A and B are not both —CO—, $R^7$ is $C_1$–$C_5$ alkyl, Z is —$CH_2$—, —O—, —S—, or —$N(R^8)$—, $R^8$ is H or $C_1$–$C_6$ alkyl, and n is 1 or 2.

2. The compound according to claim 1, wherein $R^4$ and $R^5$ are independently H, $C_1$–$C_5$-alkyl, or $R^4$ and $R^5$ taken together with the nitrogen to which they are both bound form 1-pyrrolidinyl, 1-piperidinyl, or 1-azepanyl, or $R^4$ and $R^5$ taken together with the nitrogen to which they are both bound are:

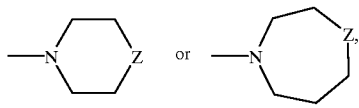

and Z is —S— or —O—.

3. A compound according to claim 1 selected from the group consisting of 2-((2-(Azaperhydroepinylcarbonylamino)-4-methylpentyl)amino)-N-(tert-butyl)-3-(4-(phenylmethoxy)phenyl)-(2S)-propanamide;

[S-(R*,R*)]-Azepane-1-carboxylic acid {1-[2-(4-benzyloxy-phenyl)-1-tert-butoxy-methyl-ethylcarbamoyl]-3-methyl-butyl}-amide;

[S-(R*,R*)]Azepane-1-carboxylic acid (1-{[2-(4-benzyloxy-phenyl)-1-tert-butyl-carbamoyl-ethylamino]-methyl}-3-methyl-butyl)-amide;

[S-(R*,R*)]-2-Dimethylamino-4-methyl-pentanoic acid [2-(4-benzyloxy-phenyl)-1-morpholin-4-ylmethyl-ethyl]-amide;

[S-(R*,R*)]-Azepane-1-carboxylic acid {1-[2-(4-benzyloxy-phenyl)-1-morpholin-4-ylmethyl-ethylcarbamoyl]-3-methyl-butyl}-amide;

[S-(R*,R*)]Azepane-1-carboxylic acid {1-[2-(4-benzyloxy-phenyl)-1-(tert-butyl-amino-methyl)-ethylcarbamoyl]-3-methyl-butyl}-amide;

(S,S)-Azepane-1-carboxylic acid {1-[2-(4-benzyloxy-phenyl)-1-diethylaminomethyl-ethylcarbamoyl]-3-methyl-butyl}-amide;

(S)-2-(2-Amino-4-methyl-pentylamino)-3-(4-benzyloxy-phenyl)-N-tert-butyl-propionamide; and 2-(2-Amino-4-methyl-pentylamino)-3-(4-benzyloxy-phenyl)-N-tert-butyl-propionamide.

4. A therapeutic composition comprising an effective calcium channel blocking amount of the compound of claim 1 with a pharmaceutically acceptable carrier.

5. A therapeutic composition comprising an effective amount of the compound of claim 1 with a pharmaceutically acceptable carrier.

6. A method of blocking calcium channels, the method comprising administering to a mammal in need of calcium channel blocking, a therapeutically effective amount of a compound of claim 1 to block calcium channels.

7. A method of blocking calcium channels, the method comprising administering to a mammal in need of calcium channel blocking, a therapeutically effective amount of a compound of claim 3 to block calcium channels.

* * * * *